United States Patent [19]

Williams

[11] Plant 4,361

[45] Jan. 2, 1979

[54] ROSE PLANT

[76] Inventor: J. Benjamin Williams, 2800 Elnora St., Silver Spring, Md. 20902

[21] Appl. No.: 875,586

[22] Filed: Feb. 6, 1978

[51] Int. Cl.[2] ..... A01H 5/00

[52] U.S. Cl. ..... Plt./20

[58] Field of Search ..... Plt./19-20

*Primary Examiner*—Robert E. Bagwill

[57] ABSTRACT

A grandiflora rose plant characterized by its unusual vigor and its brilliant, orange-red blooms.

1 Drawing Figure

1

The present invention relates to a new and distinct variety of rose plant of the grandiflora rose class which was originated by my crossing as seed parent a rose seedling derived from a cross between the rose variety known as "Queen Elizabeth" (U.S. Plant Pat. No. 1,259) and the rose variety known as "Aztec" (U.S. Plant Pat. No. 1,648), and a seedling derived from a cross between the rose variety known as "Independence" (U.S. Plant Pat. No. 1,036) and the rose variety known as "Scarlet Knight" (U.S. Plant Pat. No. 2,692).

Among the novel characteristics possessed by this new variety which distinguish it from its parents and all other varieties of which I am aware are: (1) brilliant flaming orange-red coloring of the inner petal surfaces with a heavy smoky red on outer side of petals, (2) long lasting blooms holding their color well on the plant and after cutting, having petals that drop off cleanly on aging, and (3) a vigorous plant which is "winter hardy" with large waxed reddish green foliage extremely resistant to disease and adverse weather, and produces flowers borne singly and several together as sprays. Large strong canes are produced all summer long from base of plant. Asexual reproduction by budding of the new variety as performed in Chester County, Pa., shows that the foregoing and other distinguishing characteristics come true to form and are established and transmitted through succeeding propagations.

The new and improved rose variety which I have developed is an unusually vigorous upright growing grandiflora rose with unusual brilliant fiery orange red coloring of iridescent quality. The flowers have excellent form and open well in varied weather conditions. The color of the blooms holds well and the appearance is not adversely affected by rain or heat. A strong rose attar fragrance complements the beauty of the flowers.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "45B" is plate 45B of the Royal Horticultural Society Color Chart.

Parentage: Seedling.

*Seed parent.*—Unnamed seedling from a cross of "Aztec" × "Queen Elizabeth".

2

*Pollen parent.*—Unnamed seedling from a cross of "Independence" × "Scarlet Knight".

Class: Grandiflora.

The following observations are made of specimens grown in Chester County, Pa., during the month of June.

1. FLOWER

Blooming habit: Continuous and abundant.

A. Bud:

(1) *Size.*—Medium.

(2) *Form.*—Short pointed.

(3) *Color.*—When sepals first divide — 42A with blackish orange red marking on outer side of petals. When petals begin to unfurl — 40A. When half-blown: inside of petals — 44B; reverse side of petals — 42A.

(4) *Sepals.*—Large, tapered, curling back as bud opens extending the full length of the unopen bud. Sepals color: inside — 147B; outside — near 146A with 185A overcast.

(5) *Peduncle.*—Length — 3½ to 4 inches. Strength — strong and erect. Color — near 146B completely overlaid with 185A pigmentation. Aspect — smooth with some small prickles.

B. Bloom:

(1) *Size.*—Average size when fully expanded — 4½ to 5 inches.

(2) *Borne.*—Singly and several together in sprays of 3 to 5 blooms.

(3) *Form.*—Short tapered; petals remaining at first loosely rolled outward becoming ruffled at maturity; excellent substance open, flower holds well in heat and wet weather.

(4) *Petalage.*—Number of petals under normal conditions — 34.

(5) *Color (during first two days).*—Inner petals at center of flower — 44A. Outer petals — near 44C. Base of petals (point of attachment) — 42A. Reverse of petals — 44C. General tonality from a distance — near 44B.

(6) *Color change.*—As bloom ages — center of inner petal takes on a fiery orange-red cast (43A) color holds extremely well cut or on bush. General tonality three or more days — 44B to 44C.

C. Petals:

(1) *Texture.*—Thick.

(2) *Appearance.*—Inside — velvety. Outside — satiny with dark pigmentation on outer side and tip when in bud.

(3) *Form.*—Rounded slight notching.
(4) *Arrangement.*—Imbricated, regularly arranged shingle-like.
(5) *Petaloids in center.*—Few, small.
(6) *Persistence.*—Drop off cleanly.
(7) *Fragrance.*—Strong rose attar.
(8) *Lasting quality.*—Excellent on plant and as cut flower and hold their brilliant color extremely well.

2. REPRODUCTIVE ORGANS

A. Stamens, filaments and anthers:
(1) *Arrangement.*—Medium size, regularly arranged around styles.
(2) *Color.*—22B
B. Pollen: Color — 22A.
C. Styles: Bunched, uneven, short, thin
D. Stigmas: Color — pink with cream tips
E. Hips: Shape — globular. Size — large. Color — 169A. Do seeds protrude — slight.

3. PLANT

A. Form: Upright vased shaped.
B. Growth: Very vigorous, large uniform branching on main stems new growth occurs regularly through season from base of plant. Height attained — 4 to 5 ft. in first season.
C. Foliage: Compounded 3 to 5 leaflets on single bloom, 5 to 7 leaflets on main canes.
(1) *Size.*—Large.
(2) *Quantity.*—Abundant, cover plant to ground.
(3) *Color.*—New foliage: Almost purple red, 183B. Upper side — near to 183A with deep green veining. Under side — greenish red with 183C overcast. Old foliage: Upper side — holly green somewhat near but darker than 137B. Under side — 137C.
(4) *Shape.*—Oval, pointed.
(5) *Texture.*—Upper side — leathery, glossy. Under side — smooth between ribs.
(6) *Edge.*—Serrated.
(7) *Serration.*—Very small and uniform.
(8) *Leaf Stem.*—Color — 137B. Under side — 137C.
(9) *Stipules.*—Medium smooth.
(10) *Resistance to disease.*—Blackspot — highly resistant. Mildew — highly resistant.
D. Wood:
(1) *New wood.*—Color — 136B. Bark — smooth with some fine prickles.
(2) *Old wood.*—Color — 136C. Bark — smooth with many thorns and prickles.
E. Thorns:
(1) *Thorns.*—Quantity — numerous but decorative. On laterals from stalk — numerous. Form — flat base. Length — large. Color (when young) — 136B with 185A washing. Position — irregular.
(2) *Prickles.*—Quantity — numerous. On laterals — profuse.
F. Winter hardiness: Good winter hardiness, no protection needed. Old wood scales after 2 years growth.

I claim:

1. A new and distinct variety of rose plant of the grandiflora class, substantially as shown and described, characterized particularly by recurrent flowers borne singly and in sprays of 3 to 5 blooms having fiery orange-red cast at the inner petals with a smokey red marking on tip of bud and outer petals, on a strong upright vased shaped plant of above average winter hardiness with outstanding strong disease resistance.

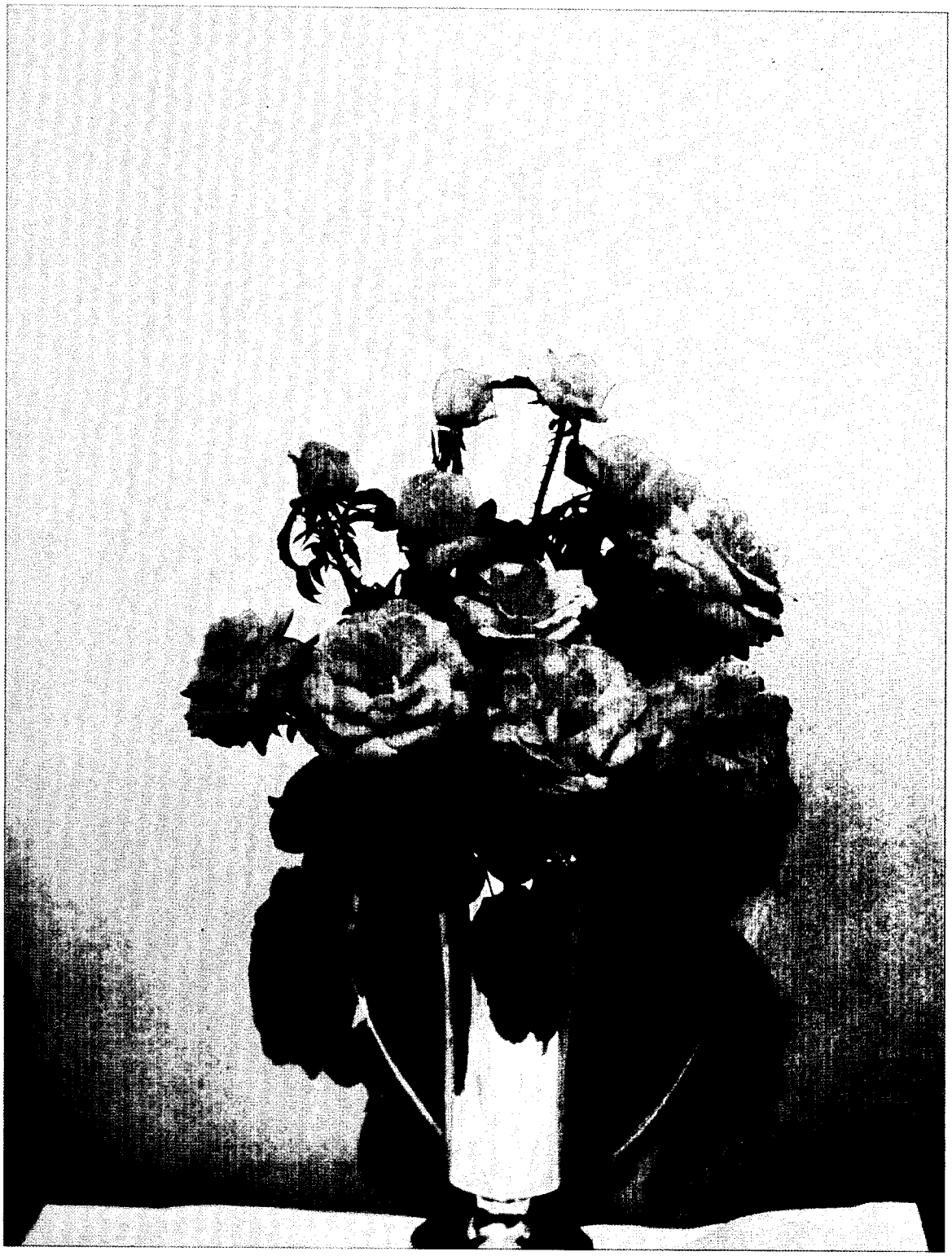

* * * * *